United States Patent
Tuomikoski et al.

(10) Patent No.: US 6,880,765 B2
(45) Date of Patent: Apr. 19, 2005

(54) SCENT LURE DISPENSER

(76) Inventors: Joseph William Tuomikoski, 44800 Bayview Dr., Novi, MI (US) 48377; David Edward Lee, 2485 Pine Lake Ave., Keego Harbor, MI (US) 48320; Dale James Syer, 1732 Ashstan Dr., Walled Lake, MI (US) 48390

( * ) Notice: Subject to any disclaimer, the term of this patent is extended or adjusted under 35 U.S.C. 154(b) by 231 days.

(21) Appl. No.: 10/037,431

(22) Filed: Oct. 29, 2001

(65) Prior Publication Data

US 2003/0080197 A1 May 1, 2003

(51) Int. Cl.⁷ .............................................. A24F 25/00
(52) U.S. Cl. ............................. 239/34; 239/53; 239/55; 239/57
(58) Field of Search ................................... 239/34–60

(56) References Cited

U.S. PATENT DOCUMENTS

| | | | |
|---|---|---|---|
| 3,000,022 A | * 9/1961 | Cathey et al. | 441/65 |
| 3,706,140 A | * 12/1972 | Brillaud et al. | 34/60 |
| 3,945,568 A | * 3/1976 | Bychowski | 239/57 |
| 4,159,631 A | * 7/1979 | Lee | 63/1.15 |
| 4,779,794 A | * 10/1988 | Moore | 232/1 B |
| 4,944,455 A | * 7/1990 | Haust et al. | 239/59 |
| 5,035,435 A | 7/1991 | Burgeson et al. | |
| 5,456,036 A | 10/1995 | Butz | |
| 5,555,663 A | 9/1996 | Burgeson | |
| 5,836,842 A | 11/1998 | McLearan | |
| 5,987,800 A | 11/1999 | Regan | |
| 6,010,540 A | * 1/2000 | Telesca et al. | 8/142 |
| 6,038,804 A | 3/2000 | Cuerrier | |
| 6,174,251 B1 | 1/2001 | Lemote | |
| 6,199,311 B1 | 3/2001 | Foster | |
| 6,237,788 B1 | * 5/2001 | Shuen | 215/12.1 |
| 6,543,365 B1 | * 4/2003 | Vasel et al. | 102/502 |

* cited by examiner

Primary Examiner—Dinh Q. Nguyen
(74) Attorney, Agent, or Firm—Foster, Swift, Collins & Smith, P.C.

(57) ABSTRACT

The invention is a reusable scent lure dispenser. One embodiment can be made of a variety of materials, large enough to throw, comprising two hemispherical body members, each having a planar flange extending along and attached to their outer periphery, a releasable means to couple the body members by their flanges, and a means along the flanges' outer peripheries to form an airtight seal against one another, one body member also having scent openings on its flange within the means to form an airtight seal, and can include a scent carrier disposed within the interior of one of the body members. The lure dispenser can be colored for various appropriate applications. Reflective material may be attached to the exposed surfaces of the hemispherical body members to allow easy retrieval at night. A tab with a mounting hole can allow easy hanging, such as in a tree.

6 Claims, 3 Drawing Sheets

SCENT LURE DISPENSER

BACKGROUND OF THE INVENTION

1. Field of the Invention

The present invention relates generally to scent lures, and more particularly to an improved method and system to dispense the scent lure.

2. Discussion of the Prior Art

It has long been known that animals, such as game animals like deer, elk and bear, are naturally drawn to certain natural scents, such as the urine or various hormones of the same species of animal. Examples include doe estrous, doe urine, buck urine, skunk urine, fox urine, and bobcat urine or any other appropriate game scent. People often use these scents to attract the animals into their vicinity for hunting, photography or observation.

Typically, the scent is in a liquid form and may be used in any of a variety of ways. One method is to pour the liquid scent lure onto absorbent pads such as felt, which are then hung on branches or twigs. The scent is allowed to vaporize into the ambient air to attract the animals. Another method is to pour the liquid scent lure onto trees or on the ground at either real or artificially created scrapes where a horned animal might mark his territory. Liquid scents may also be dripped in a controlled manner on either real or artificial scrapes.

Devices to dispense scent lures are well known in the prior art. See generally, U.S. Pat. No. 5,456,036 to Butz; U.S. Pat. No. 5,555,663 to Burgeson; U.S. Pat. No. 5,836,842 to McLearnan; U.S. Pat. No. 5,987,800 to Regan; U.S. Pat. No. 6,174,251 to Lemote; U.S. Pat. No. 6,038,804 to Cuerrier; and U.S. Pat. No. 6,199,311 to Foster.

Conventional methods of applying scents require the user to walk to a given location and apply the scent or scent-dispensing device. This method requires the hunter to walk to each location to be scented causing human scent and noise to be introduced in all areas traversed. Human scent and noise typically repel animals thus defeating the intended purpose of the lure.

Attempts are known in the prior art to dispense scent lures within a given area without introducing undesirable human scents in the process. These can include scented arrows or exploding pellets fired from a pistol designed for that use. Here too are disadvantages in that they are complicated, expensive, non-reusable, create unnecessary and unwanted noise, require additional equipment, or require a large amount of force to break open a pellet.

For example, the Foster device requires a biodegradable, non-reusable pellet to be propelled with a force sufficient to break open on impact. This device requires some sort of additional device to propel the pellet, a hard surface to strike it upon, or both.

Unfortunately, an inexpensive, simple, reusable, easy to retrieve, and versatile scent lure dispenser that addresses these mentioned deficiencies is unknown in the prior art. Thus, there is a need for an improved scent lure dispenser to overcome the disadvantages found in the prior art.

SUMMARY OF THE INVENTION

Accordingly, the present invention provides an improved scent lure dispenser. It has many advantages and novel features not anticipated, rendered obvious, suggested, or even implied by any of the prior art scent lure dispensers.

One embodiment of the present invention generally comprises a scent lure dispenser made of wood or plastic or other materials approximately 2 to 3 inches in diameter comprising a center axis, two hemispherical body members, each having a planar flange extending along and attached to their outer periphery, a releasable means to couple the body members by their flanges, and a means along the flanges' outer peripheries to form an airtight seal against one another, one body member also having scent openings on its flange within the means to form an airtight seal, and can include a scent carrier such as felt disposed within the interior of one of the body members.

Additional features of the present invention are also present. The lure dispenser can be colored for various appropriate applications such as green, orange, or camouflage. Reflective material may be attached to the exposed surfaces of the hemispherical body members to allow easy retrieval at night. A tab can be added to allow easy hanging, such as off a tree.

The means to couple the first and second body members in one embodiment comprises a threaded bore on one flange along the center axis and extended into the first body member interior; and a threaded rod on the other flange adjacent to and configured to couple to the threaded bore on the center axis.

The means along the outer peripheries to form an airtight seal against the second body member comprises an "O" ring and annular grooves along the outer peripheries to receive the "O" ring.

The present invention provides an improved scent lure dispenser that can be easily, economically, and efficiently manufactured and marketed.

The present invention provides an improved scent lure dispenser that is of a durable, reliable construction, reusable, easily retrievable day or night, and versatile.

The present invention is simple to use and deploy without the user having to traverse to the area deployed, thereby not introducing undesirable human scents or noise.

Other objects of the present invention will become more apparent to persons having ordinary skill in the art to which the present invention pertains from the following description taken in conjunction with the accompanying figures.

BRIEF DESCRIPTION OF THE FIGURES

The foregoing objects, advantages, and features, as well as other objects and advantages, will become apparent with reference to the description and figures below, in which like numerals represent like elements and in which.

DETAILED DESCRIPTION OF THE PREFERRED EMBODIMENT

Figure 1:
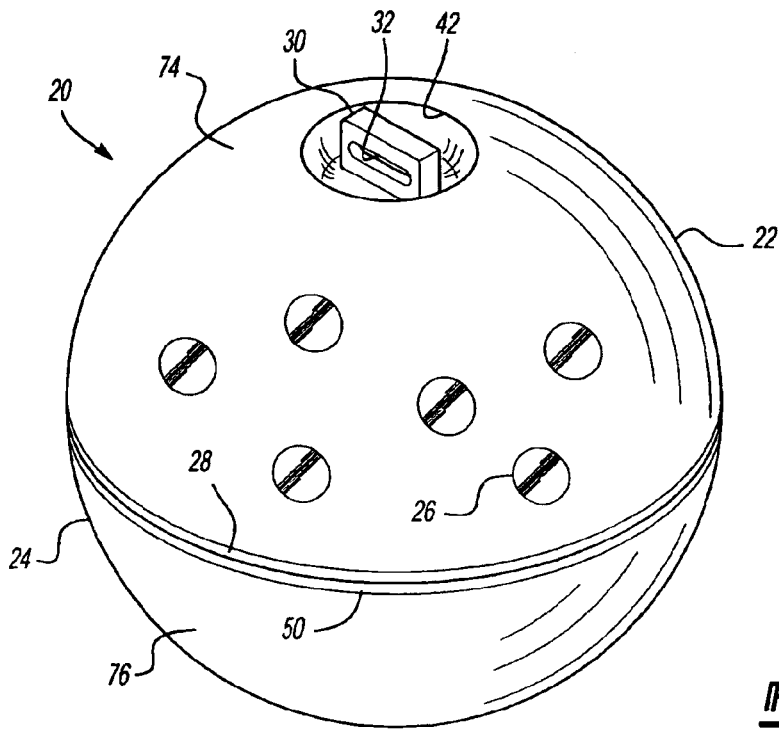
FIG. 1 illustrates a perspective view of the scent lure dispenser of the present invention in a closed position.

The present invention relates to an improved scent lure dispenser (deployer or disperser) that can be easily, economically, and efficiently manufactured and marketed. It is durable, reliably constructed, reusable, easily retrievable day or night, and versatile. The present invention is simple to use and deploy without the user having to traverse to the area deployed, thereby not introducing undesirable human scents or noise.

Referring to the figures, one possible embodiment of the present scent lure dispenser is illustrated generally as lure dispenser 20. In a typical configuration, the lure dispenser 20 can be about two to three inches in diameter and can have a first hemispherical body member 22 and a second hemispherical body member 24. The goal is to make the lure dispenser 20 small enough to fit in your pocket, yet large enough to allow accurate throwing. Further, the lure dispenser 20 is designed to be scent free and to conserve a scent when not in use.

The lure dispenser 20 is versatile in that it can be deployed in a number of manners such as throwing or merely hanging from a tree. It is best to throw the lure dispenser 20 from the ground. The user should also use gloves to reduce the amount of human scent introduced to the lure dispenser 20.

The first body member 22 has a first body member inner surface 68 defining a first body member interior 70, a first body member exposed surface 74 and a first outer periphery 40 that has a planar first flange 28 extending along and attached to the first outer periphery 40. Also, the first body member 22 has a bore 42 located at a lure dispenser center axis 44 having a tab 30 extending upwardly within the bore 42. The tab 30 also has an opening 32. The tab 30 can be used to assist in sealing the scent as described below and the opening 32 allows easy hanging of the lure dispenser 20 from a tree and the like if desired. In the center of the first flange 28 and extending into the first body member interior 70 along the lure dispenser center axis 44 is a threaded bore 46. The first flange 28 also has an first flange exposed surface 48. Near the outside diameter of the first flange exposed surface 48 is a first annular groove 34 for receiving a portion of an "O" ring 36.

The second body member 24 has a second body member inner surface 64 defining a second body member interior 72, a second body member exposed surface 76, a second outer periphery 54 that has a planar second flange 50 extending along and attached to the second outer periphery 54. Also attached to the second body member 24 along the lure dispenser center axis 44 is a threaded rod 38 configured to screw into the threaded bore 46 thereby securely holding or fastening the two body members together. Many other possible configurations to hold the two body members together are possible and the embodiment shown in the figures is just one way to illustrate the invention.

Figure 2:
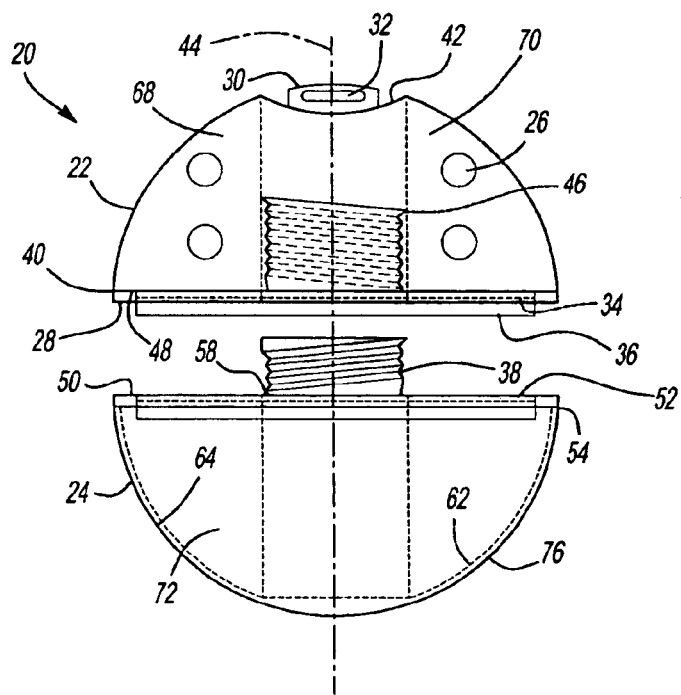
FIG. 2 illustrates a side view of the scent lure dispenser of the present invention in its open position.
Figure 3:
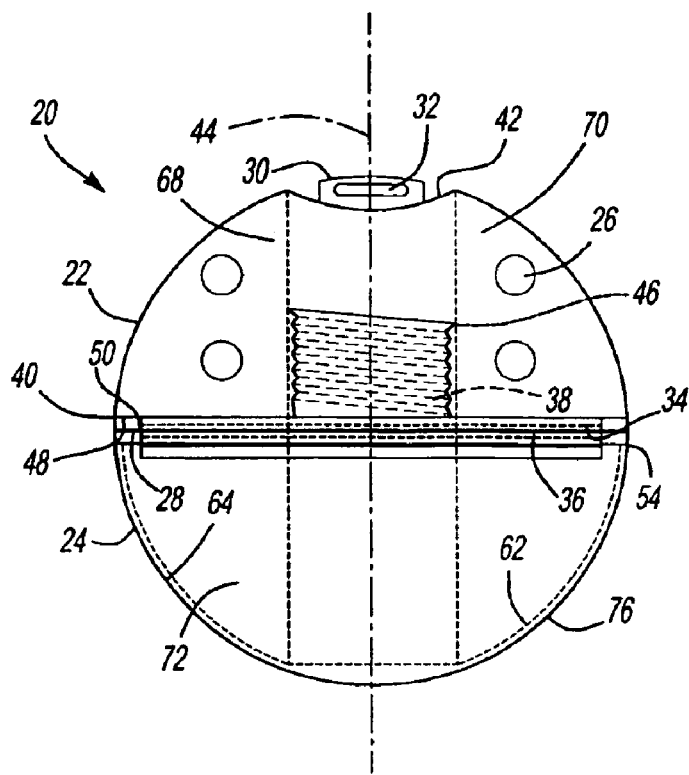
FIG. 3 illustrates a side view of the scent lure dispenser of the present invention in its closed position.
Figure 4:
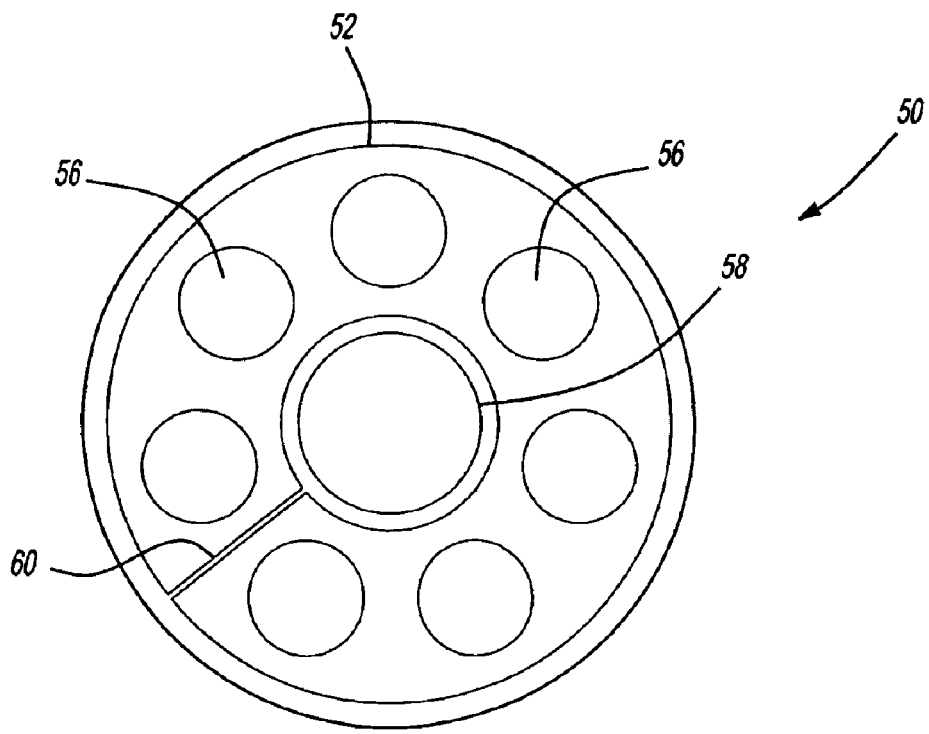
FIG. 4 illustrates a top view of a second flange for the present invention.

The features of the second flange 50 are more easily seen in the top view of FIG. 4. The figure shows the second flange 50 can have a second annular groove 52 corresponding in position to be adjacent to the "O" ring 36 (shown on the first flange 28 in FIG. 2) when the two body members are securely held together, thereby creating an airtight seal to prolong the life of the scent disposed within. Also, the second flange 50 has a plurality of scent openings 56 arranged around a second flange center opening 58 but within the "O" ring 36 diameter. For this illustrated embodiment, the scent openings are circular. The threaded rod 38 extends through the center opening 58 towards the threaded bore 46. The second flange 50 also has a slit 60 to allow wick replacement as discussed below.

The second body member 24 can hold an easily removable optional scent carrier such as an absorbent wick that allows dispensing through gradual evaporation. A scent (not shown) can be applied to the absorbent wick using a variety of methods known in the art. The scents used can vary based on the game the user wishes to lure. Some examples include any pre-rut, rut, or post-rut scents, animal scents, as well as other scents such as clover scents, apples, acorns, oranges, cedar, earth. If the desired scent is a gel or solid, the use of the scent carrier can be optional.

Figure 5A:
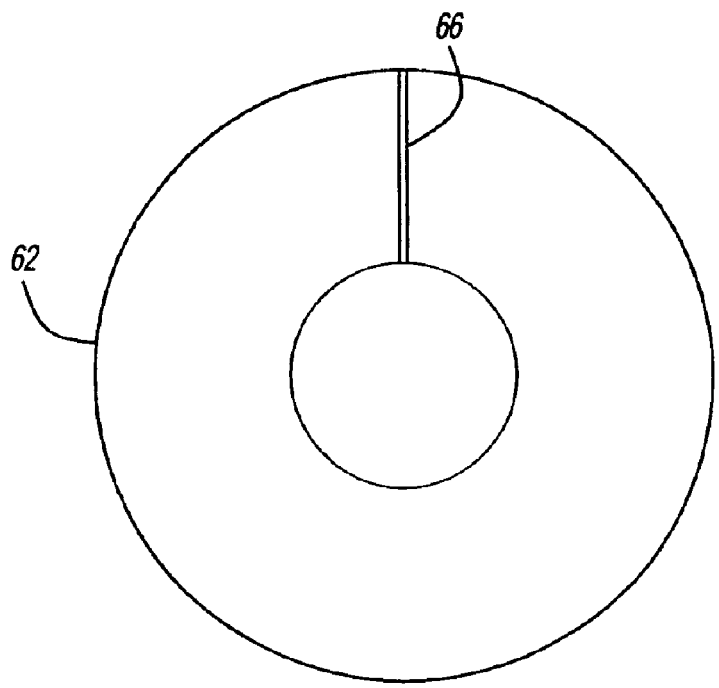
FIG. 5 illustrates top and side views of a scent carrier (wick) of the present invention.
Figure 5B:
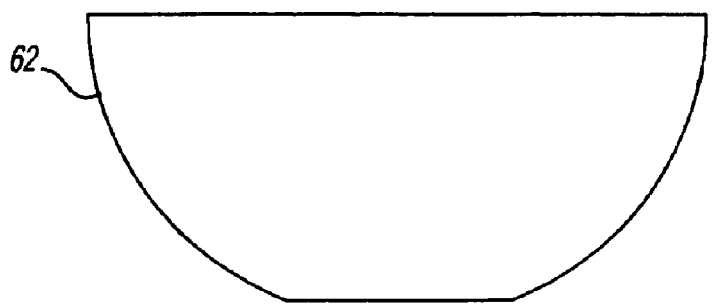

In the embodiment illustrated, a scent carrier is included and is a wick 62 disposed within the second body member interior 72. The wick 62 of the illustrated embodiment is shown in FIG. 5 though many possible wick shapes and configurations are possible. The wick 62 has a wick slit 66 to allow easy insertion and removal into the second body member 24 inner cavity. Once the wick 62 is inserted, and the two body members arranged in the open position, the user using gloved hands can apply the scent by an eyedropper or other methods. The wick 62 can be made of felt, wool, cotton, or other suitable materials.

The lure dispenser 20 can then be closed airtight by the "O" ring 36 for transport to the intended site. Once there, the user can unscrew the two body members allowing the scent to escape via the scent openings 56 and placing the lure dispenser 20 by either hanging or throwing. When use is discontinued, the two body members can be screwed back together to form an airtight seal to prevent unwanted evaporation.

The lure dispenser 20 can be made from a variety of materials such as plastic or wood. The lure dispenser 20 can also be made in a variety of colors to alternately allow easy retrieval day or night or camouflage depending on the user's preferred application. In an embodiment where the lure dispenser 20 is green or any number of camouflage patterns, it can be hung from a tree near a scrape or thrown to an area beneficial to hunting the game. An orange embodiment can be thrown anywhere the game will intercept the scent. Additionally, retrieval can be made easier, especially at night, by adding reflective material known in the prior art. The embodiment illustrated uses adhesive reflective dots 26, which can be added in any number of configurations on the first body member exposed surface 74 and second body member exposed surface 76.

With respect to the above description, it is to be realized that optimum dimensional relationships for the parts of the invention, include variations in size, materials, shape, form, function and manner of operation, assembly and use. They are deemed readily apparent and obvious to one skilled in the art, and all equivalent relationships to those illustrated in the drawings and described in the specification are intended to be encompassed by the present invention. The above-described embodiments of the invention are provided purely for purposes of example. Many other variations, modifications, and applications of the invention may be made.

We claim:

1. A scent lure dispenser comprising:

a center axis;

a first hemispherical body member;

a second hemispherical body member;

the first hemispherical body member comprising a first body member inner surface defining an interior of the first hemispherical body member, a first body member exposed surface, a first outer periphery, a planar first flange extending along and attached to the first outer periphery, a releasable means to couple to the second hemispherical body member, and a means along the first outer periphery to form an airtight seal against the second hemispherical body member;

the second hemispherical body member comprising a second body member inner surface defining an interior of the second hemispherical body member, a second body member exposed surface, a second outer periphery, a planar second flange extending along and attached to the second outer periphery, a releasable means to couple to the first hemispherical body member, a means along the second outer peiphery to form an airtight seal against the first hemispherical body member, the planar second flange further comprising scent openings within the means to form an airtight seal; and wherein the first hemispherical body member further comprises a bore at the center axis, a tab extending upwardly within up through the bore at the center axis, and the tab further comprising an opening.

2. A scent lure dispenser comprising:

a center axis;

a first hemispherical body member;

a second hemispherical body member;

the first hemispherical body member comprising a first body member inner surface defining an interior of the first hemispherical body member, a first body member exposed surface, a first outer periphery, a planar first flange extending along and attached to the first outer periphery, a releasable means to couple to the second hemispherical body member, and a means along the first outer periphery to form an airtight seal against the second hemispherical body member;

the second hemispherical body member comprising a second body member inner surface defining an interior of the second hemispherical body member, a second body member exposed surface, a second outer periphery, a planar second flange extending along and attached to the second outer periphery, a releasable means to couple to the first hemispherical body member, a means along the second outer periphery to form an airtight seal against the first hemispherical body member, the planar second flange further comprising scent openings within the means to form an airtight seal; and wherein the releasable means to couple the first and second hemispherical body members comprises a threaded bore on the first flange along the center axis and extended into the first body member interior; and a threaded rod on the second flange adjacent to and configured to couple to the threaded bore on the center axis.

3. A scent lure dispenser comprising:

a center axis;

a first hemispherical body member;

a second hemispherical body member;

the first hemispherical body member comprising a first body member inner surface defining an interior of the first hemispherical body member, a first body member exposed surface, a first outer periphery, a planar first flange extending along and attached to the first outer periphery, a releasable means to couple to the second hemispherical body member, and a means along the first outer periphery to form an airtight seal against the second hemispherical body member;

the second hemispherical body member comprising a second body member inner surface defining an interior of the second hemispherical body member, a second body member exposed surface, a second outer periphery, a planar second flange extending along and attached to the second outer periphery, a releasable means to couple to the first hemispherical body member, a means along the second outer periphery to form an airtight seal against the first hemispherical body member, the planar second flange further comprising scent openings within the means to form an airtight seal; and wherein the scent openings comprise a plurality of circular openings evenly spaced around a second flange center opening.

4. A scent lure dispenser comprising:

a center axis;

a first hemispherical body member;

a second hemispherical body member;

the first hemispherical body member comprising a first body member inner surface defining an interior of the first hemispherical body member, a first body member exposed surface, a first outer periphery, a planar first flange extending along and attached to the first outer periphery, a releasable means to couple to the second hemispherical body member, and a means along the first outer periphery to form an airtight seal against the second hemispherical body member;

the second hemispherical body member comprising a second body member inner surface defining an interior of the second hemispherical body member, a second body member exposed surface, a second outer periphery, a planar second flange extending along and attached to the second outer periphery, a releasable means to couple to the first hemispherical body member, a means along the second outer periphery to form an airtight seal against the first hemispherical body member, the planar second flange further comprising scent openings within the means to form an airtight seal; and wherein the first hemispherical body member further comprises a bore at the center axis, a tab extending upwardly within the bore at the center axis, and the tab further comprising an opening.

5. A scent lure dispenser comprising:

a center axis;

a first hemispherical body member;

a second hemispherical body member;

the first hemispherical body member comprising a first body member inner surface defining an interior of the first hemispherical body member, a first body member exposed surface, a first outer periphery, a planar first flange extending along and attached to the first outer periphery, a releasable means to couple to the second hemispherical body member, and a means along the first outer periphery to form an airtight seal against the second hemispherical body member;

the second hemispherical body member comprising a second body member inner surface defining an interior of the second hemispherical body member, a second body member exposed surface, a second outer periphery, a planar second flange extending along and attached to the second outer periphery, a releasable means to couple to the first hemispherical body member, a means along the second outer periphery to form an airtight seal against the first hemispherical body member, the planar second flange further comprising scent openings within the means to form an airtight seal; and wherein the releasable means to couple the first and second hemispherical body members comprises a threaded bore on the first flange along the center axis and extended into the first body member interior; and a threaded rod on the second flange adjacent to and configured to couple to the threaded bore on the center axis.

6. A scent lure dispenser comprising:

a center axis;

a first hemispherical body member;

a second hemispherical body member;

the first hemispherical body member comprising a first body member inner surface defining an interior of the first hemispherical body member, a first body member exposed surface, a first outer periphery, a planar first flange extending along and attached to the first outer periphery, a releasable means to couple to the second hemispherical body member, and a means along the first outer periphery to form an airtight seal against the second hemispherical body member;

the second hemispherical body member comprising a second body member inner surface defining an interior of the second hemispherical body member, a second body member exposed surface, a second outer periphery, a planar second flange extending along and attached to the second outer periphery, a releasable means to couple to the first hemispherical body member, a means along the second outer periphery to form an airtight seal against the first hemispherical body member, the planar second flange further comprising scent openings within the means to form an airtight seal; and wherein the scent openings comprise a plurality of circular openings evenly spaced around a second flange center opening.

* * * * *